United States Patent
Ralph et al.

(10) Patent No.: US 8,029,568 B2
(45) Date of Patent: *Oct. 4, 2011

(54) INTERVERTEBRAL SPACER DEVICE HAVING A SLOTTED PARTIAL CIRCULAR DOMED ARCH STRIP SPRING

(75) Inventors: James D. Ralph, Seaside Park, NJ (US); Stephen Tatar, Montville, NJ (US); Joseph P. Errico, Green Brook, NJ (US)

(73) Assignee: SpineCore, Inc., Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/829,724

(22) Filed: Jul. 2, 2010

(65) Prior Publication Data

US 2010/0268342 A1    Oct. 21, 2010

Related U.S. Application Data

(63) Continuation of application No. 10/648,464, filed on Aug. 25, 2003, now abandoned, which is a continuation of application No. 10/035,669, filed on Nov. 9, 2001, now Pat. No. 6,610,092, which is a continuation-in-part of application No. 09/982,148, filed on Oct. 18, 2001, now Pat. No. 6,673,113.

(51) Int. Cl.
 *A61F 2/44* (2006.01)
(52) U.S. Cl. .............. 623/17.13; 623/17.14; 623/17.15
(58) Field of Classification Search .............. 623/623, 623/17.13–17.16
See application file for complete search history.

(56) References Cited

U.S. PATENT DOCUMENTS

| | | | |
|---|---|---|---|
| 916,421 A | 3/1909 | Crittenden | |
| 1,518,205 A | 12/1924 | Burt | |
| 1,539,221 A | 5/1925 | Tennant | |
| 1,882,462 A | 10/1932 | Weber | |
| 2,121,682 A | 6/1938 | Boucher | |
| 2,127,424 A | 8/1938 | Rolle | |
| 2,193,122 A * | 3/1940 | Crabbs | 200/255 |
| 2,319,992 A | 5/1943 | Hubbard | |
| 2,669,896 A | 2/1954 | Clough | |
| 2,719,688 A | 10/1955 | Seifert | |
| 3,195,380 A | 7/1965 | Bicks | |
| 3,278,107 A | 10/1966 | Rygg | |
| 3,326,254 A | 6/1967 | Diehl | |
| 3,486,505 A | 12/1969 | Morrison | |
| 3,604,487 A | 9/1971 | Gilbert | |
| 3,659,661 A | 5/1972 | Young et al. | |

(Continued)

FOREIGN PATENT DOCUMENTS

DE    2263842A A1    7/1974

(Continued)

OTHER PUBLICATIONS

International Search Report, PCT/US2009/002530, dated Jul. 10, 2009.

(Continued)

*Primary Examiner* — David H Willse
*Assistant Examiner* — Javier Blanco
(74) *Attorney, Agent, or Firm* — Lerner, David, Littenberg, Krumholz & Mentlik, LLP

(57) ABSTRACT

An intervertebral spacer device having a pair of opposing plates for seating against opposing vertebral bone surfaces. Each of the opposing plates has an external surface with a deflectable wire mesh thereon, into which the bone can readily grow.

9 Claims, 4 Drawing Sheets

U.S. PATENT DOCUMENTS

| | | |
|---|---|---|
| 3,679,244 A | 7/1972 | Reddy |
| 3,743,042 A | 7/1973 | Hilterhaus |
| 3,867,728 A | 2/1975 | Stubstad et al. |
| 3,948,141 A | 4/1976 | Shinjo |
| 4,077,618 A | 3/1978 | Durant |
| 4,105,407 A | 8/1978 | Sanderson |
| 4,263,903 A | 4/1981 | Griggs |
| 4,303,001 A | 12/1981 | Trungold |
| 4,303,268 A | 12/1981 | Davidson |
| 4,309,777 A | 1/1982 | Patil |
| 4,317,387 A | 3/1982 | Myers et al. |
| 4,457,484 A | 7/1984 | Hameister |
| 4,528,980 A | 7/1985 | Kenna |
| 4,531,517 A | 7/1985 | Forte et al. |
| 4,566,466 A | 1/1986 | Ripple et al. |
| 4,605,417 A | 8/1986 | Fleischauer |
| 4,759,766 A | 7/1988 | Buettner-Janz et al. |
| 4,759,769 A | 7/1988 | Hedman et al. |
| 4,917,704 A | 4/1990 | Frey et al. |
| 4,932,969 A | 6/1990 | Frey et al. |
| 4,955,908 A | 9/1990 | Frey et al. |
| 4,968,010 A | 11/1990 | Odobasic |
| 4,969,907 A | 11/1990 | Koch et al. |
| 4,997,432 A | 3/1991 | Keller |
| 5,002,576 A * | 3/1991 | Fuhrmann et al. ......... 623/17.15 |
| 5,015,247 A | 5/1991 | Michelson |
| 5,030,219 A | 7/1991 | Matsen, III et al. |
| 5,034,254 A * | 7/1991 | Cologna et al. ................ 428/63 |
| 5,112,178 A | 5/1992 | Overhues et al. |
| 5,122,130 A | 6/1992 | Keller |
| 5,192,327 A | 3/1993 | Brantigan |
| 5,236,460 A | 8/1993 | Barber |
| 5,258,007 A | 11/1993 | Spetzler et al. |
| 5,258,031 A | 11/1993 | Salib et al. |
| 5,306,308 A | 4/1994 | Gross et al. |
| 5,306,309 A | 4/1994 | Wagner et al. |
| 5,314,477 A | 5/1994 | Marnay |
| 5,370,697 A | 12/1994 | Baumgartner |
| 5,376,120 A | 12/1994 | Sarver et al. |
| 5,401,269 A | 3/1995 | Buttner-Janz et al. |
| 5,405,400 A | 4/1995 | Linscheid et al. |
| 5,425,773 A | 6/1995 | Boyd et al. |
| 5,443,514 A | 8/1995 | Steffee |
| 5,458,641 A | 10/1995 | Ramirez Jimenez |
| 5,458,642 A | 10/1995 | Beer et al. |
| 5,507,816 A | 4/1996 | Bullivant |
| 5,514,180 A | 5/1996 | Heggeness et al. |
| 5,534,029 A | 7/1996 | Shima |
| 5,548,642 A | 8/1996 | Diethorn |
| 5,549,690 A | 8/1996 | Hollister et al. |
| 5,556,431 A | 9/1996 | Buttner-Janz |
| 5,556,432 A | 9/1996 | Kubein-Meesenburg et al. |
| 5,562,736 A | 10/1996 | Ray et al. |
| 5,562,738 A | 10/1996 | Boyd et al. |
| 5,571,109 A | 11/1996 | Bertagnoli |
| 5,593,456 A | 1/1997 | Merlette |
| 5,599,279 A | 2/1997 | Slotman et al. |
| 5,645,605 A | 7/1997 | Klawitter |
| 5,653,762 A | 8/1997 | Pisharodi |
| 5,667,347 A | 9/1997 | Matthews |
| 5,674,295 A | 10/1997 | Ray et al. |
| 5,674,296 A | 10/1997 | Bryan et al. |
| 5,676,701 A | 10/1997 | Yuan et al. |
| 5,676,702 A | 10/1997 | Ratron |
| 5,683,399 A | 11/1997 | Jones |
| 5,683,464 A | 11/1997 | Wagner et al. |
| 5,683,465 A | 11/1997 | Shinn et al. |
| 5,718,254 A | 2/1998 | Murphy |
| 5,720,751 A | 2/1998 | Jackson |
| 5,732,992 A | 3/1998 | Mauldin |
| 5,733,290 A | 3/1998 | McCue et al. |
| 5,749,916 A | 5/1998 | Richelsoph |
| 5,755,796 A | 5/1998 | Ibo et al. |
| 5,755,798 A | 5/1998 | Papavero et al. |
| 5,766,252 A | 6/1998 | Henry et al. |
| 5,769,856 A | 6/1998 | Dong et al. |
| 5,776,198 A | 7/1998 | Rabbe et al. |
| 5,782,830 A | 7/1998 | Farris |
| 5,782,832 A | 7/1998 | Larsen et al. |
| 5,827,328 A | 10/1998 | Buttermann |
| 5,860,990 A | 1/1999 | Nobles et al. |
| 5,865,846 A | 2/1999 | Bryan et al. |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 5,910,141 A | 6/1999 | Morrison et al. |
| 5,916,267 A | 6/1999 | Tienboon |
| 5,926,685 A | 7/1999 | Krebs et al. |
| 5,928,284 A | 7/1999 | Mehdizadeh |
| 5,976,186 A | 11/1999 | Bao et al. |
| 5,983,889 A | 11/1999 | Thomas |
| 5,989,291 A | 11/1999 | Ralph et al. |
| 5,989,294 A | 11/1999 | Marlow |
| 6,001,030 A | 12/1999 | Delaney |
| 6,001,130 A | 12/1999 | Bryan et al. |
| 6,019,792 A | 2/2000 | Cauthen |
| 6,039,763 A | 3/2000 | Shelokov |
| 6,050,999 A | 4/2000 | Paraschac et al. |
| 6,051,751 A | 4/2000 | Sioshansi et al. |
| 6,063,088 A | 5/2000 | Winslow |
| 6,063,121 A | 5/2000 | Xavier et al. |
| 6,066,174 A | 5/2000 | Farris |
| 6,066,175 A | 5/2000 | Henderson et al. |
| 6,080,155 A | 6/2000 | Michelson |
| 6,093,205 A | 7/2000 | McLeod et al. |
| 6,093,207 A | 7/2000 | Pisharodi |
| 6,096,080 A | 8/2000 | Nicholson et al. |
| 6,106,557 A | 8/2000 | Robioneck et al. |
| 6,111,222 A | 8/2000 | Hattori |
| 6,113,367 A | 9/2000 | Dunaevsky et al. |
| 6,113,602 A | 9/2000 | Sand |
| 6,113,637 A | 9/2000 | Gill et al. |
| 6,113,638 A | 9/2000 | Williams et al. |
| 6,113,639 A | 9/2000 | Ray et al. |
| 6,136,031 A | 10/2000 | Middleton |
| 6,139,550 A | 10/2000 | Michelson |
| 6,143,012 A | 11/2000 | Gausepohl |
| 6,146,421 A | 11/2000 | Gordon et al. |
| 6,156,067 A | 12/2000 | Bryan et al. |
| 6,159,211 A | 12/2000 | Boriani et al. |
| 6,159,215 A | 12/2000 | Urbahns et al. |
| 6,162,252 A | 12/2000 | Kuras et al. |
| 6,174,311 B1 | 1/2001 | Branch et al. |
| 6,179,873 B1 | 1/2001 | Zientek |
| 6,179,874 B1 | 1/2001 | Cauthen |
| 6,190,413 B1 | 2/2001 | Sutcliffe |
| 6,190,414 B1 | 2/2001 | Young et al. |
| 6,193,757 B1 | 2/2001 | Foley et al. |
| 6,213,055 B1 | 4/2001 | Willinger et al. |
| 6,214,005 B1 | 4/2001 | Benzel et al. |
| 6,214,049 B1 | 4/2001 | Gayer et al. |
| 6,224,607 B1 | 5/2001 | Michelson |
| 6,228,023 B1 | 5/2001 | Zaslavsky et al. |
| 6,228,118 B1 | 5/2001 | Gordon |
| 6,231,609 B1 | 5/2001 | Mehdizadeh |
| 6,235,034 B1 | 5/2001 | Bray |
| 6,235,060 B1 | 5/2001 | Kubein-Meesenburg et al. |
| 6,241,732 B1 | 6/2001 | Overaker et al. |
| 6,241,769 B1 | 6/2001 | Nicholson et al. |
| 6,261,293 B1 | 7/2001 | Nicholson et al. |
| 6,261,296 B1 | 7/2001 | Aebi et al. |
| 6,261,324 B1 | 7/2001 | Merlette |
| 6,277,149 B1 | 8/2001 | Boyle et al. |
| 6,280,458 B1 | 8/2001 | Boche et al. |
| 6,296,647 B1 | 10/2001 | Robioneck et al. |
| 6,296,665 B1 | 10/2001 | Strnad et al. |
| 6,308,483 B1 | 10/2001 | Romine |
| 6,319,257 B1 | 11/2001 | Carignan et al. |
| 6,325,828 B1 | 12/2001 | Dennis et al. |
| 6,342,057 B1 | 1/2002 | Brace et al. |
| 6,348,071 B1 | 2/2002 | Steffee et al. |
| 6,368,350 B1 | 4/2002 | Erickson et al. |
| 6,375,682 B1 | 4/2002 | Fleischmann et al. |
| 6,395,030 B1 | 5/2002 | Songer et al. |
| 6,395,032 B1 | 5/2002 | Gauchet |

| | | | | | | |
|---|---|---|---|---|---|---|
| 6,395,035 B2 | 5/2002 | Bresina et al. | | 6,908,484 B2 | 6/2005 | Zubok et al. |
| 6,413,259 B1 | 7/2002 | Lyons et al. | | 6,918,934 B2 | 7/2005 | Ralph et al. |
| 6,416,551 B1 | 7/2002 | Keller | | 6,923,814 B1 | 8/2005 | Hildebrand et al. |
| 6,428,544 B1 | 8/2002 | Ralph et al. | | 6,981,990 B2 | 1/2006 | Keller |
| 6,432,106 B1 | 8/2002 | Fraser | | 6,989,032 B2 | 1/2006 | Errico et al. |
| 6,436,102 B1 | 8/2002 | Ralph et al. | | 6,991,654 B2 | 1/2006 | Foley |
| 6,440,168 B1 | 8/2002 | Cauthen | | 7,008,432 B2 | 3/2006 | Schlapfer et al. |
| 6,447,547 B1 | 9/2002 | Michelson | | 7,011,684 B2 | 3/2006 | Eckman |
| 6,461,359 B1 | 10/2002 | Tribus et al. | | 7,022,139 B2 | 4/2006 | Errico et al. |
| 6,468,310 B1 | 10/2002 | Ralph et al. | | 7,025,787 B2 | 4/2006 | Bryan et al. |
| 6,471,725 B1 | 10/2002 | Ralph et al. | | 7,048,764 B2 | 5/2006 | Ferree |
| 6,478,796 B2 | 11/2002 | Zucherman et al. | | 7,060,099 B2 | 6/2006 | Carli et al. |
| 6,478,800 B1 | 11/2002 | Fraser et al. | | 7,063,725 B2 | 6/2006 | Foley |
| 6,478,801 B1 | 11/2002 | Ralph et al. | | 7,066,959 B2 | 6/2006 | Errico et al. |
| 6,488,710 B2 | 12/2002 | Besselink | | 7,070,598 B2 | 7/2006 | Lim et al. |
| 6,517,580 B1 | 2/2003 | Ramadan et al. | | 7,083,651 B2 | 8/2006 | Diaz et al. |
| 6,520,996 B1 | 2/2003 | Manasas et al. | | 7,087,055 B2 | 8/2006 | Lim et al. |
| 6,524,312 B2 | 2/2003 | Landry et al. | | 7,115,132 B2 | 10/2006 | Errico et al. |
| 6,527,320 B1 | 3/2003 | Gregg | | 7,118,579 B2 | 10/2006 | Michelson |
| 6,527,786 B1 | 3/2003 | Davis et al. | | 7,118,580 B1 | 10/2006 | Beyersdorff et al. |
| 6,527,804 B1 | 3/2003 | Gauchet et al. | | 7,122,055 B2 | 10/2006 | Ralph et al. |
| 6,527,806 B2 | 3/2003 | Ralph et al. | | 7,125,425 B2 | 10/2006 | Foley et al. |
| 6,540,785 B1 | 4/2003 | Gill et al. | | 7,153,325 B2 | 12/2006 | Kim et al. |
| 6,551,316 B1 | 4/2003 | Rinner et al. | | 7,160,327 B2 | 1/2007 | Errico et al. |
| 6,554,864 B2 | 4/2003 | Ralph et al. | | 7,169,182 B2 | 1/2007 | Errico et al. |
| 6,562,047 B2 | 5/2003 | Ralph et al. | | 7,214,244 B2 | 5/2007 | Zubok et al. |
| 6,562,073 B2 | 5/2003 | Foley | | 7,223,291 B2 | 5/2007 | Errico et al. |
| 6,572,653 B1 | 6/2003 | Simonson | | 7,235,081 B2 | 6/2007 | Errico et al. |
| 6,576,017 B2 | 6/2003 | Foley et al. | | 7,235,082 B2 | 6/2007 | Bartish et al. |
| 6,579,290 B1 | 6/2003 | Hardcastle et al. | | 7,238,203 B2 | 7/2007 | Bagga et al. |
| 6,579,320 B1 | 6/2003 | Gauchet et al. | | 7,270,680 B2 | 9/2007 | Ralph et al. |
| 6,579,321 B1 | 6/2003 | Gordon et al. | | 7,326,216 B2 | 2/2008 | Bertagnoli et al. |
| 6,582,466 B1 | 6/2003 | Gauchet | | 7,491,241 B2 | 2/2009 | Errico et al. |
| 6,582,468 B1 | 6/2003 | Gauchet | | 7,635,368 B2 | 12/2009 | Errico et al. |
| 6,589,247 B2 | 7/2003 | McGahan et al. | | 7,713,302 B2 | 5/2010 | Ralph et al. |
| 6,592,624 B1 | 7/2003 | Fraser et al. | | 2001/0005796 A1 | 6/2001 | Zdeblick et al. |
| 6,605,093 B1 | 8/2003 | Blake | | 2001/0007073 A1 | 7/2001 | Zucherman et al. |
| 6,607,558 B2 | 8/2003 | Kuras | | 2001/0010001 A1 | 7/2001 | Michelson |
| 6,607,559 B2 | 8/2003 | Ralph et al. | | 2001/0012938 A1 | 8/2001 | Zucherman et al. |
| 6,610,092 B2 | 8/2003 | Ralph et al. | | 2001/0016773 A1 | 8/2001 | Serhan et al. |
| 6,610,093 B1 | 8/2003 | Pisharodi | | 2001/0016774 A1 | 8/2001 | Bresina et al. |
| 6,623,525 B2 | 9/2003 | Ralph et al. | | 2001/0020170 A1 | 9/2001 | Zucherman et al. |
| 6,632,091 B1 | 10/2003 | Cise et al. | | 2001/0027343 A1 | 10/2001 | Keller |
| 6,641,614 B1 | 11/2003 | Wagner et al. | | 2001/0039452 A1 | 11/2001 | Zucherman et al. |
| 6,645,248 B2 | 11/2003 | Casutt | | 2002/0017789 A1 | 2/2002 | Holmes et al. |
| 6,645,249 B2 | 11/2003 | Ralph et al. | | 2002/0035400 A1 | 3/2002 | Bryan et al. |
| 6,652,233 B2 | 11/2003 | Otake | | 2002/0045901 A1 | 4/2002 | Wagner et al. |
| 6,652,525 B1 | 11/2003 | Assaker et al. | | 2002/0045904 A1 | 4/2002 | Fuss et al. |
| 6,652,533 B2 | 11/2003 | O'Neil | | 2002/0062131 A1 | 5/2002 | Gallo |
| 6,666,866 B2 | 12/2003 | Martz et al. | | 2002/0082597 A1 | 6/2002 | Fraser |
| 6,669,699 B2 | 12/2003 | Ralph et al. | | 2002/0082695 A1 | 6/2002 | Neumann |
| 6,669,730 B2 | 12/2003 | Ralph et al. | | 2002/0082701 A1 | 6/2002 | Zdeblick et al. |
| 6,669,731 B2 | 12/2003 | Ralph et al. | | 2002/0084562 A1 | 7/2002 | Kelsey |
| 6,669,732 B2 | 12/2003 | Serhan et al. | | 2002/0099377 A1 | 7/2002 | Zucherman et al. |
| 6,673,113 B2 | 1/2004 | Ralph et al. | | 2002/0107571 A1 | 8/2002 | Foley |
| 6,679,887 B2 | 1/2004 | Nicholson et al. | | 2002/0107572 A1 | 8/2002 | Foley et al. |
| 6,679,915 B1 | 1/2004 | Cauthen | | 2002/0111679 A1 | 8/2002 | Zucherman et al. |
| 6,682,562 B2 | 1/2004 | Viart et al. | | 2002/0111681 A1 | 8/2002 | Ralph et al. |
| 6,692,495 B1 | 2/2004 | Zacouto | | 2002/0111682 A1 | 8/2002 | Ralph et al. |
| 6,706,068 B2 | 3/2004 | Ferree | | 2002/0111683 A1 | 8/2002 | Ralph et al. |
| 6,709,439 B2 | 3/2004 | Rogers et al. | | 2002/0111684 A1 | 8/2002 | Ralph et al. |
| 6,712,819 B2 | 3/2004 | Zucherman et al. | | 2002/0111685 A1 | 8/2002 | Ralph et al. |
| 6,712,825 B2 | 3/2004 | Aebi et al. | | 2002/0111686 A1 | 8/2002 | Ralph et al. |
| 6,716,245 B2 | 4/2004 | Pasquet et al. | | 2002/0111687 A1 | 8/2002 | Ralph et al. |
| 6,723,127 B2 | 4/2004 | Ralph et al. | | 2002/0116009 A1 | 8/2002 | Fraser et al. |
| 6,733,532 B1 | 5/2004 | Gauchet et al. | | 2002/0123750 A1 | 9/2002 | Eisermann et al. |
| 6,752,832 B2 | 6/2004 | Neumann | | 2002/0128714 A1 | 9/2002 | Manasas et al. |
| 6,755,841 B2 | 6/2004 | Fraser et al. | | 2002/0128715 A1 | 9/2002 | Bryan et al. |
| 6,764,515 B2 | 7/2004 | Ralph et al. | | 2002/0143399 A1 | 10/2002 | Sutcliffe |
| 6,793,678 B2 | 9/2004 | Hawkins | | 2002/0147450 A1 | 10/2002 | LeHuec et al. |
| 6,800,093 B2 | 10/2004 | Nicholson et al. | | 2002/0161375 A1 | 10/2002 | Ralph et al. |
| 6,821,298 B1 | 11/2004 | Jackson | | 2002/0169508 A1 | 11/2002 | Songer et al. |
| 6,827,743 B2 | 12/2004 | Eisermann et al. | | 2002/0177897 A1 | 11/2002 | Michelson |
| 6,835,206 B2 | 12/2004 | Jackson | | 2002/0188295 A1 | 12/2002 | Martz et al. |
| 6,837,905 B1 | 1/2005 | Lieberman | | 2002/0193880 A1 | 12/2002 | Fraser |
| 6,863,688 B2 | 3/2005 | Ralph et al. | | 2003/0009223 A1 | 1/2003 | Fehling et al. |
| 6,863,689 B2 | 3/2005 | Ralph et al. | | 2003/0009224 A1 | 1/2003 | Kuras |
| 6,875,213 B2 | 4/2005 | Michelson | | 2003/0014057 A1 | 1/2003 | Ralph et al. |
| 6,887,274 B2 | 5/2005 | Ralph et al. | | 2003/0014109 A1 | 1/2003 | Ralph et al. |

| | | |
|---|---|---|
| 2003/0014110 A1 | 1/2003 | Ralph et al. |
| 2003/0014111 A1 | 1/2003 | Ralph et al. |
| 2003/0014112 A1 | 1/2003 | Ralph et al. |
| 2003/0014113 A1 | 1/2003 | Ralph et al. |
| 2003/0014114 A1 | 1/2003 | Ralph et al. |
| 2003/0014115 A1 | 1/2003 | Ralph et al. |
| 2003/0014116 A1 | 1/2003 | Ralph et al. |
| 2003/0023245 A1 | 1/2003 | Ralph et al. |
| 2003/0023309 A1 | 1/2003 | Ralph et al. |
| 2003/0023310 A1 | 1/2003 | Ralph et al. |
| 2003/0028197 A1 | 2/2003 | Hanson et al. |
| 2003/0028249 A1 | 2/2003 | Baccelli et al. |
| 2003/0028252 A1 | 2/2003 | Ralph et al. |
| 2003/0040796 A1 | 2/2003 | Ferree |
| 2003/0040801 A1 | 2/2003 | Ralph et al. |
| 2003/0045939 A1 | 3/2003 | Casutt |
| 2003/0055503 A1 | 3/2003 | O'Neil |
| 2003/0060886 A1 | 3/2003 | Van Hoeck et al. |
| 2003/0065395 A1 | 4/2003 | Ralph et al. |
| 2003/0069586 A1 | 4/2003 | Errico et al. |
| 2003/0069642 A1 | 4/2003 | Ralph et al. |
| 2003/0074064 A1 | 4/2003 | Gerbec et al. |
| 2003/0074067 A1 | 4/2003 | Errico et al. |
| 2003/0078662 A1 | 4/2003 | Ralph et al. |
| 2003/0078663 A1 | 4/2003 | Ralph et al. |
| 2003/0078664 A1 | 4/2003 | Ralph et al. |
| 2003/0078665 A1 | 4/2003 | Ralph et al. |
| 2003/0078666 A1 | 4/2003 | Ralph et al. |
| 2003/0078667 A1 | 4/2003 | Manasas et al. |
| 2003/0078668 A1 | 4/2003 | Michelson |
| 2003/0083747 A1 | 5/2003 | Winterbottom et al. |
| 2003/0083749 A1 | 5/2003 | Kuslich et al. |
| 2003/0093153 A1 | 5/2003 | Banick et al. |
| 2003/0100949 A1 | 5/2003 | Michelson |
| 2003/0100951 A1 | 5/2003 | Serhan et al. |
| 2003/0109928 A1 | 6/2003 | Pasquet et al. |
| 2003/0120344 A1 | 6/2003 | Michelson |
| 2003/0125739 A1 | 7/2003 | Bagga et al. |
| 2003/0125748 A1 | 7/2003 | Li et al. |
| 2003/0135278 A1 | 7/2003 | Eckman |
| 2003/0135279 A1 | 7/2003 | Michelson |
| 2003/0149438 A1 | 8/2003 | Nichols et al. |
| 2003/0149482 A1 | 8/2003 | Michelson |
| 2003/0167091 A1 | 9/2003 | Scharf |
| 2003/0167092 A1 | 9/2003 | Foley |
| 2003/0171813 A1 | 9/2003 | Kiester |
| 2003/0176921 A1 | 9/2003 | Lawson |
| 2003/0176922 A1 | 9/2003 | Lawson et al. |
| 2003/0176923 A1 | 9/2003 | Keller et al. |
| 2003/0176925 A1 | 9/2003 | Paponneau |
| 2003/0181982 A1 | 9/2003 | Kuslich |
| 2003/0187453 A1 | 10/2003 | Schlapfer et al. |
| 2003/0187454 A1 | 10/2003 | Gill et al. |
| 2003/0187508 A1 | 10/2003 | Cauthen |
| 2003/0191533 A1 | 10/2003 | Dixon et al. |
| 2003/0191534 A1 | 10/2003 | Viart et al. |
| 2003/0195514 A1 | 10/2003 | Trieu et al. |
| 2003/0195632 A1 | 10/2003 | Foley et al. |
| 2003/0199981 A1 | 10/2003 | Ferree |
| 2003/0199983 A1 | 10/2003 | Michelson |
| 2003/0204260 A1 | 10/2003 | Ferree |
| 2003/0208271 A1 | 11/2003 | Kuras |
| 2003/0208273 A1 | 11/2003 | Eisermann et al. |
| 2003/0208274 A1 | 11/2003 | Davis |
| 2003/0216744 A1 | 11/2003 | Longhini et al. |
| 2003/0216810 A1 | 11/2003 | Ralph et al. |
| 2003/0220690 A1 | 11/2003 | Cauthen |
| 2003/0220694 A1 | 11/2003 | Cauthen |
| 2003/0225408 A1 | 12/2003 | Nichols et al. |
| 2003/0225416 A1 | 12/2003 | Bonvallet et al. |
| 2003/0229358 A1 | 12/2003 | Errico et al. |
| 2003/0229397 A1 | 12/2003 | Davis |
| 2003/0233097 A1 | 12/2003 | Ferree |
| 2003/0233145 A1 | 12/2003 | Landry et al. |
| 2003/0233148 A1 | 12/2003 | Ferree |
| 2003/0236520 A1 | 12/2003 | Lim et al. |
| 2004/0002758 A1 | 1/2004 | Landry et al. |
| 2004/0002759 A1 | 1/2004 | Ferree |
| 2004/0002761 A1 | 1/2004 | Rogers et al. |
| 2004/0002762 A1 | 1/2004 | Hawkins |
| 2004/0006343 A1 | 1/2004 | Sevrain |
| 2004/0010254 A1 | 1/2004 | Cook et al. |
| 2004/0010316 A1 | 1/2004 | William et al. |
| 2004/0021042 A1 | 2/2004 | Stephen et al. |
| 2004/0022582 A1 | 2/2004 | Sick |
| 2004/0024406 A1 | 2/2004 | Ralph et al. |
| 2004/0024407 A1 | 2/2004 | Ralph et al. |
| 2004/0024459 A1 | 2/2004 | Ferree |
| 2004/0024461 A1 | 2/2004 | Ferree |
| 2004/0024462 A1 | 2/2004 | Ferree et al. |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0034426 A1 | 2/2004 | Errico et al. |
| 2004/0059343 A1 | 3/2004 | Shearer et al. |
| 2004/0068318 A1 | 4/2004 | Coates et al. |
| 2004/0068320 A1 | 4/2004 | Robie et al. |
| 2004/0078079 A1 | 4/2004 | Foley |
| 2004/0106927 A1 | 6/2004 | Ruffner et al. |
| 2004/0117022 A1 | 6/2004 | Marnay et al. |
| 2004/0133281 A1 | 7/2004 | Khandkar et al. |
| 2004/0138750 A1 | 7/2004 | Mitchell |
| 2004/0143332 A1 | 7/2004 | Krueger et al. |
| 2004/0148027 A1 | 7/2004 | Errico et al. |
| 2004/0148028 A1 | 7/2004 | Ferree et al. |
| 2004/0158325 A1 | 8/2004 | Errico et al. |
| 2004/0167535 A1 | 8/2004 | Errico et al. |
| 2004/0167628 A1 | 8/2004 | Foley |
| 2004/0204762 A1 | 10/2004 | Ralph et al. |
| 2004/0215198 A1 | 10/2004 | Marnay et al. |
| 2004/0220567 A1 | 11/2004 | Eisermann et al. |
| 2004/0220582 A1 | 11/2004 | Keller |
| 2004/0233148 A1 | 11/2004 | Tanghe et al. |
| 2004/0243240 A1 | 12/2004 | Beaurain et al. |
| 2004/0267369 A1 | 12/2004 | Lyons et al. |
| 2005/0033430 A1 | 2/2005 | Powers et al. |
| 2005/0043803 A1 | 2/2005 | Schultz et al. |
| 2005/0119665 A1 | 6/2005 | Keller |
| 2005/0131542 A1 | 6/2005 | Benzel et al. |
| 2005/0159819 A1 | 7/2005 | McCormack et al. |
| 2005/0177171 A1 | 8/2005 | Wetzler et al. |
| 2005/0182416 A1 | 8/2005 | Lim et al. |
| 2005/0256577 A1 | 11/2005 | Baumgartner et al. |
| 2005/0283237 A1 | 12/2005 | Zucherman et al. |
| 2006/0064107 A1 | 3/2006 | Bertagnoli et al. |
| 2006/0074432 A1 | 4/2006 | Stad et al. |
| 2006/0241643 A1 | 10/2006 | Lim et al. |
| 2007/0016221 A1 | 1/2007 | Beyersdorff et al. |
| 2007/0106388 A1 | 5/2007 | Michelson |
| 2007/0123907 A1 | 5/2007 | Weber |
| 2007/0161991 A1 | 7/2007 | Altarac et al. |
| 2007/0198092 A1 | 8/2007 | Errico et al. |
| 2007/0233143 A1 | 10/2007 | Josse et al. |
| 2007/0239162 A1 | 10/2007 | Bhatnagar et al. |
| 2007/0260315 A1 | 11/2007 | Foley et al. |

FOREIGN PATENT DOCUMENTS

| | | |
|---|---|---|
| DE | 3023492 A1 | 2/1982 |
| DE | 3722893 C1 | 6/1988 |
| DE | 43 15 757 | 11/1994 |
| DE | 199 03 763 A1 | 8/2000 |
| DE | 20004812 U1 | 9/2000 |
| DE | 10130825 A1 | 3/2002 |
| EP | 0369603 A1 | 5/1990 |
| EP | 0 392 076 A1 | 10/1990 |
| EP | 0 599 419 A2 | 6/1994 |
| EP | 599419 A2 | 6/1994 |
| EP | 1 222 903 A1 | 7/2002 |
| EP | 1219266 A1 | 7/2002 |
| EP | 1946709 A1 | 7/2008 |
| FR | 2 718 635 A1 | 10/1995 |
| FR | 2 730159 A1 | 8/1996 |
| FR | 2 805 985 A1 | 9/2001 |
| FR | 2 824 261 A1 | 11/2002 |
| RU | 1560184 | 4/1990 |
| RU | 2 077 288 C1 | 4/1997 |
| WO | 91/13598 A1 | 9/1991 |

| | | | |
|---|---|---|---|
| WO | 94/04100 A1 | 3/1994 |
| WO | 97/10776 A2 | 3/1997 |
| WO | 9929271 A1 | 6/1999 |
| WO | 01/01893 A1 | 1/2001 |
| WO | 01/01894 A1 | 1/2001 |
| WO | 01/62191 A2 | 8/2001 |
| WO | 01/93785 | 12/2001 |
| WO | 01/93786 A2 | 12/2001 |
| WO | 02/071986 A2 | 9/2002 |
| WO | 03/084449 A1 | 10/2003 |
| WO | 2004/019828 A1 | 3/2004 |
| WO | 2004/026186 A1 | 4/2004 |

OTHER PUBLICATIONS

Surgical Technique Using FRA Spacer Instruments, Technique Guide, Synthes Spine, 1998.

* cited by examiner

INTERVERTEBRAL SPACER DEVICE HAVING A SLOTTED PARTIAL CIRCULAR DOMED ARCH STRIP SPRING

CROSS-REFERENCE TO RELATED APPLICATION

This application is a continuation U.S. application Ser. No. 10/648,464 filed Aug. 25, 2003, now abandoned, which is a continuation of U.S. application Ser. No. 10/035,669 filed Nov. 9, 2001, now U.S. Pat. No. 6,610,092, which is a continuation-in-part of U.S. application Ser. No. 09/982,148 filed Oct. 18, 2001, now U.S. Pat. No. 6,673,113, the disclosures of which are incorporated herein by reference.

FIELD OF THE INVENTION

This invention relates generally to a spinal implant assembly for implantation into the intervertebral space between adjacent vertebral bones to simultaneously provide stabilization and continued flexibility and proper anatomical motion.

BACKGROUND OF THE INVENTION

The bones and connective tissue of an adult human spinal column consists of more than 20 discrete bones coupled sequentially to one another by a tri-joint complex which consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes which can result in spinal pathologies for which surgical intervention may be necessary. A variety of systems have been disclosed in the art which achieve immobilization and/or fusion of adjacent bones by implanting artificial assemblies in or on the spinal column. The region of the back which needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 1 and 2, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 2 the pair of cages 10 are inserted between the fifth lumbar vertebra (L5) and the top of the sacrum (S1). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional material, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the present invention to provide a new and novel intervertebral spacer which stabilizes the spine without promoting a bone fusion across the intervertebral space.

It is further an object of the present invention to provide an implant device which stabilizes the spine while still permitting normal motion.

It is further an object of the present invention to provide a device for implantation into the intervertebral space which does not promote the abnormal distribution of biomechanical stresses on the patient's spine.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a flexible intervertebral spacer device comprising a pair of spaced apart base plates, arranged in a substantially parallel planar alignment (or slightly offset relative to one another in accordance with proper lordotic angulation) and coupled to one another by means of at least one spring mechanism. This at least one spring mechanism provides a strong restoring force when a compressive load is applied to the plates, and may also permit limited rotation of the two plates relative to one another. While there are a wide variety of embodiments contemplated, one preferred embodiment is described herein as representative of preferred types.

More particularly, with respect to the base plates, which are largely similar in all embodiments, as the assembly is to be positioned between the facing surfaces of adjacent vertebral bodies, and as such need to have substantially flat external surfaces which seat against the opposing bone surfaces. Inasmuch as these bone surfaces are often concave, it is anticipated that the opposing plates may be convex in accordance with the average topology of the spinal anatomy. In addition, the plates are to mate with the bone surfaces in such a way as to not rotate relative thereto. (The plates rotate relative to one another, but not with respect to the bone surfaces to which they are each in contact with.) In order to prevent rotation of a plate relative to the bone, the upper and lower plates alternatively may each include outwardly directed spikes or ridges which penetrate the bone surface and mechanically hold the plates in place. However, it is more preferably anticipated that the plates should include a porous coating into which the bone of the vertebral body can grow. The most desirable upper and lower plate surface porous feature is a deflectable wire mesh into which the bone can readily grow, and which mesh will deform to seat into the concave upper and lower bone faces. (Note that this limited fusion of the bone to the base plate does not extend across the intervertebral space.) These features, while being preferred are not required.

Between the base plates, on the exterior of the device, there may also be included a circumferential wall which is resilient and which simply prevents vessels and tissues from entering within the interior of the device. This resilient wall may comprise a porous fabric or a semi-impermeable elastomeric material. Suitable tissue compatible materials meeting the simple mechanical requirements of flexibility and durability are prevalent in a number of medical fields including cardiovascular medicine, wherein such materials are utilized for venous and arterial wall repair, or for use with artificial valve replacements. Alternatively, suitable plastic materials are utilized in the surgical repair of gross damage to muscles and organs. Still further materials which could be utilized herein may be found in the field of orthopedic in conjunction with ligament and tendon repair. It is anticipated that future developments in this area will produce materials which are compatible for use with this invention, the breadth of which shall not be limited by the choice of such a material. For the purposes of this description, however, it shall be understood that such a circumferential wall is unnecessary, and in some instances may be a hindrance, and thusly is not included in the specific embodiment set forth hereinbelow.

As introduced above, the internal structure of the present invention comprises a spring member, or other equivalent subassembly which provides a restoring force when compressed. It is desirable that the restoring forces be directed outward against the opposing plates, when a compressive load is applied to the plates. More particularly, the restoring force providing subassembly comprises a circular slotted arch-shaped metal spring which is secured to the lower plate and against movement therefrom at its lateral ends. The slotted arched pieces of metal comprise continuous flat ends disposed at the circumferential edge, and a slotted curvate central portion. The curvate central portion is curvate in two axes, and shall hereinafter be termed a partial circular domed arch. The central portion is curved along the long axis (the length) of the strip into an upside down U-shape. The central portion is further curved in the lateral direction (the width of the strip) such that the outer surface (the top of the upside down U-shape) is convex. Stated alternatively, the central curvate portion of the metal strip comprises a section of a hemispheric shell (or paraboloid, or other suitable geometric shape) which has been cut along two minor arcs which are parallel to, but on opposing sides of a diameter (great circles) of the surface. In the preferred embodiment described herein, the majority of the hemispheric shell remains intact, having only spiral slots formed therein.

The slots formed in the curvate portion extend along the length of the strip from the junction with the flat lateral ends up to points near to the peak of the partial circular domed arch. These slots permit the spring to deflect more easily than a continuous structure, thus permitting the design to more nearly approximate the loading profile of naturally occurring intervertebral disc cartilage.

More particularly, the slotted partial circular domed arch portions of the strips deflect under loading, but provide a restoring force in opposition to the loading until they are permitted to regain their original shape. The restoring force of an arched strip of metal is proportional to the elastic properties of the material as well as the length and arc of the curvate central portion of the strip. The elasticity of the metal, which endures and counteracts the strain of the material, causes a deflection in the height of the arch.

In the preferred embodiment, the peak of the slotted partial circular domed arch further comprises a socket for flexibly coupling to a post member on the interior surface of the opposing plate. This socket is formed at the center of the central portion, which is an unslotted region. This post couples to the spring to form a ball and socket joint at the peak of the partial circular domed arch, which joint permits the plates to rotate relative to one another. This rotation may be constrained by the specific conformation of the joint such that the plates are free to rotate through only a range of angles.

More particularly, this embodiment comprises a pair of spaced apart base plates, one of which includes means for coupling the flat lateral ends of the domed arched spring thereto it (such as simple set screws). The other of the plates is similarly shaped, having a flat exterior surface (which may include a mesh or porous coating to permit bony ingrowth), but further includes a short central post portion which rises out of the interior face at a nearly perpendicular angle. The top of this short post portion includes a ball-shaped knob. The knob includes a central threaded axial bore which receives a small set screw. Prior to the insertion of the set screw, the ball-shaped head of the post can deflect radially inward (so that the ball-shaped knob contracts). The insertion of the set screw eliminates the capacity for this deflection.

As introduced above, the slotted domed arch spring is mounted to this ball-shaped knob in such a way that it may rotate freely through a range of angles equivalent to the fraction of normal human spine rotation (to mimic normal disc rotation). In order to couple with the post, the strip spring includes an socket which accommodates the ball-shaped portion of the post. More particularly, the socket includes a curvate volume having a substantially constant radius of curvature which is also substantially equivalent to the radius of the ball-shaped head of the post. The deflectability of the ball-shaped head of the post, prior to the insertion of the set screw, permits the head to be inserted into the interior volume at the center of the spring, and the washer to be rotated into the proper lordotic angulation. Subsequent introduction of the set screw into the axial bore of the post flexibly retains the head in the socket of the strip spring. This assembly provides ample spring-like performance with respect to axial compressive loads, as well as long cycle life to mimic the axial biomechanical performance of the normal human intervertebral disc.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
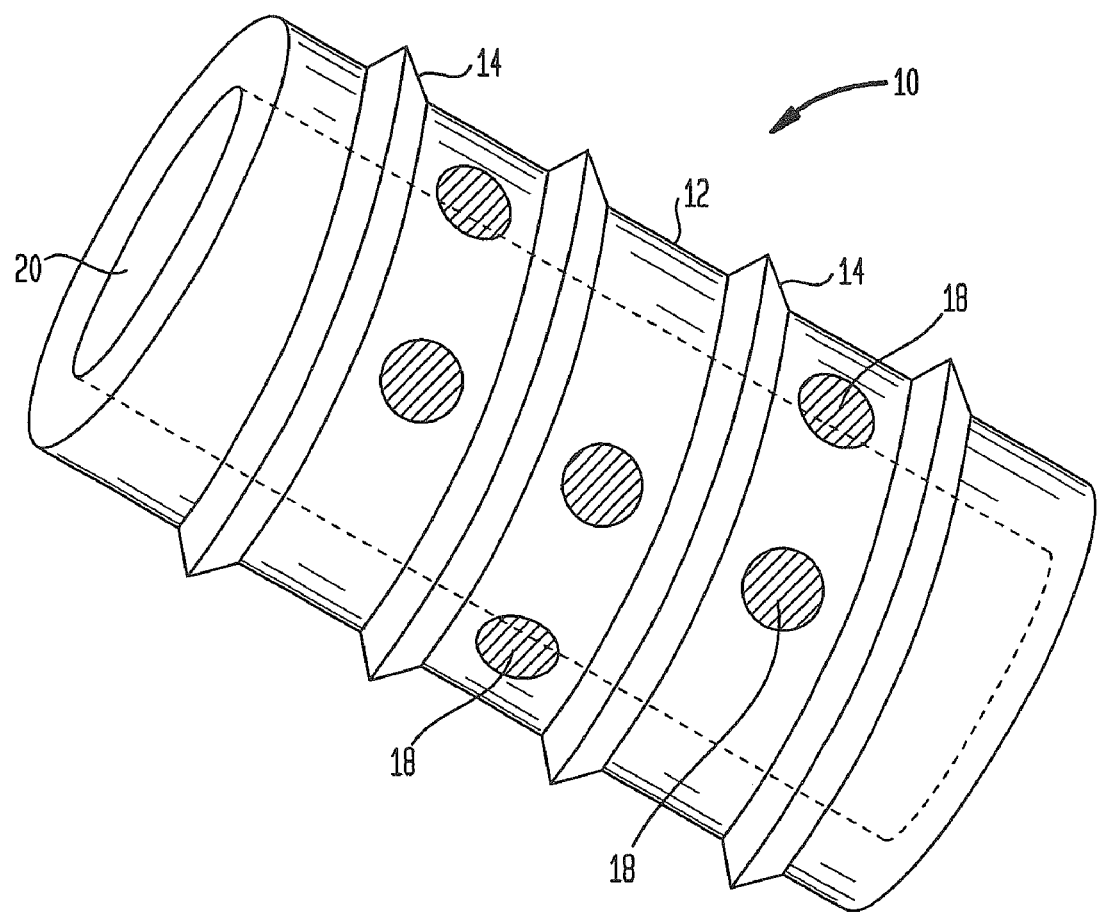
FIG. 1 is a side perspective view of an interbody fusion device of the prior art.
Figure 2:
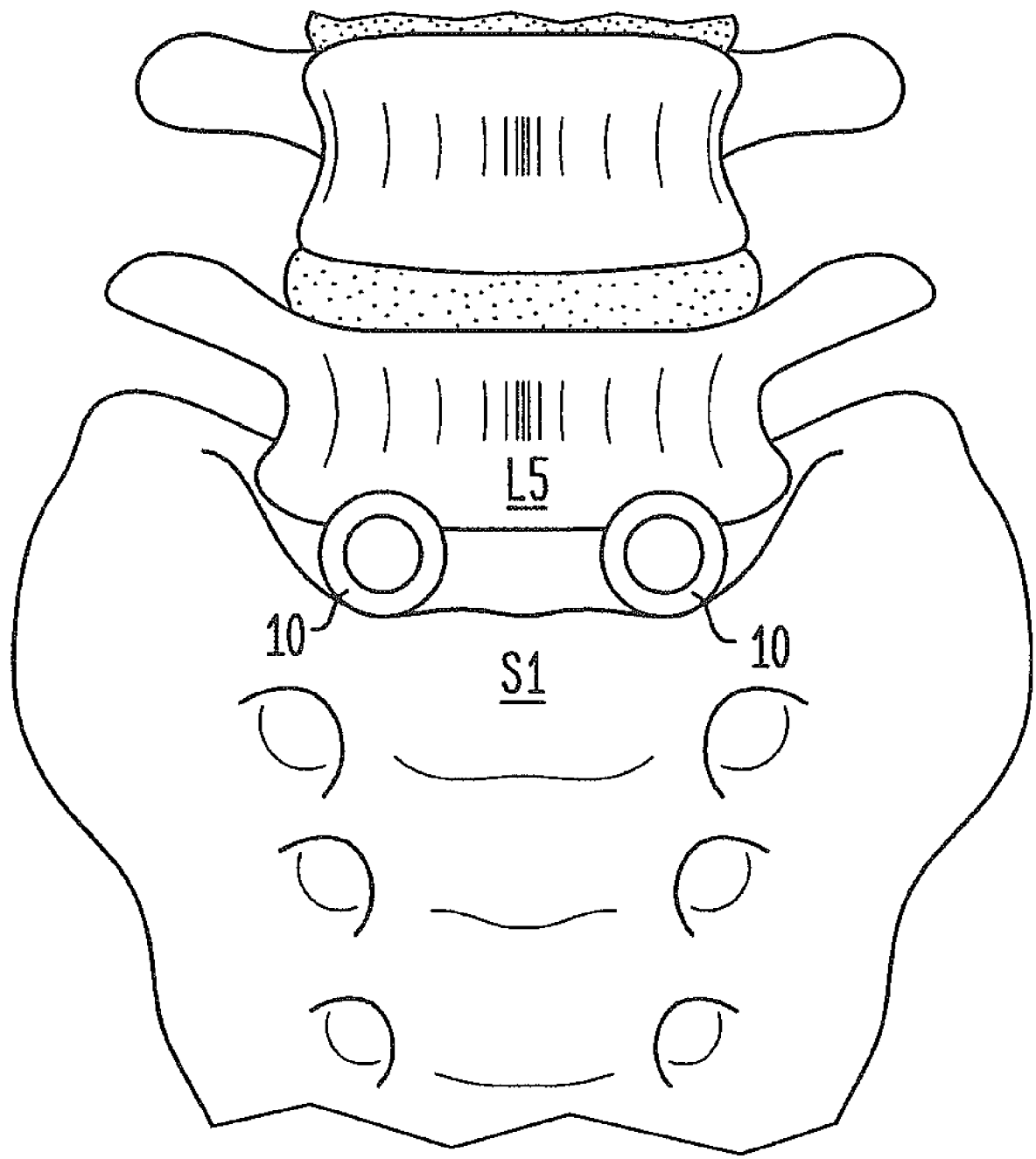
FIG. 2 is a front view of the anterior portion of the lumbosacral region of a human spine, into which a pair of interbody fusion devices of the type shown in FIG. 1 have been implanted.
Figure 3A:
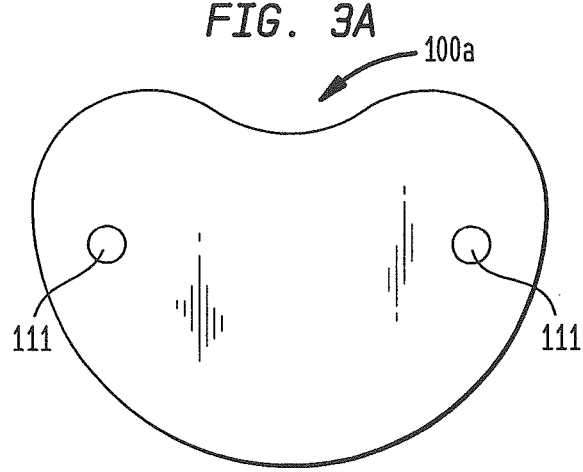
FIGS. 3a and 3b are top views of the upper and lower opposing plates of one embodiment of the present invention.
Figure 3B:
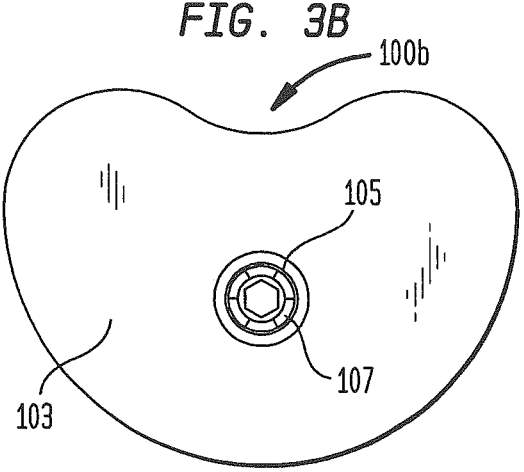

Referring now to FIGS. 3a and 3b, side cross-section views of the top and bottom plate members 100a 100b of a first embodiment of the present invention are shown. More particularly, in this embodiment, the upper and lower plates 100a, 100b are nearly identical. As the device is designed to be positioned between the facing surfaces of adjacent vertebral bodies, the plates include substantially flat surface portions 102a, 102b which seat against the opposing bone surfaces. In addition, the plates are to mate with the bone surfaces in such a way as to not rotate relative thereto. It is, therefore, preferred that the plates should include a porous coating into which the bone of the vertebral body can grow. The most desirable upper and lower plate surface porous feature is a deflectable wire mesh into which the bone can readily grow, and which mesh 104a, 104b (see FIGS. 4b and 5) will deform to seat into the concave upper and lower bone faces. (Note that this limited fusion of the bone to the base plate does not extend across the intervertebral space.)

Plate 100a further includes a single set of threaded holes 111 for receiving the set screws (shown in FIGS. 4a and 4b) required to affix the lateral ends of the domed arch strip spring thereto it.

Plate 100b has a similar shaped to the plates described above, i.e., having a flat exterior surface 102b which is designed to seat against the exposed opposing bone face in an intervertebral space, but plate 100b further includes a short central post member 105 which rises out of the interior face 103 at a nearly perpendicular angle. The top of this short post member 105 includes a ball-shaped head 107. The head 107 includes a central threaded axial bore 109 which extends down the post 105. This threaded bore 109 is designed to receive a small set screw 101. Prior to the insertion of the set screw 101, the ball-shaped head 107 of the post 105 can deflect radially inward (so that the ball-shaped head contracts). The insertion of the set screw 101 eliminates the capacity for this deflection.

Figure 4A:
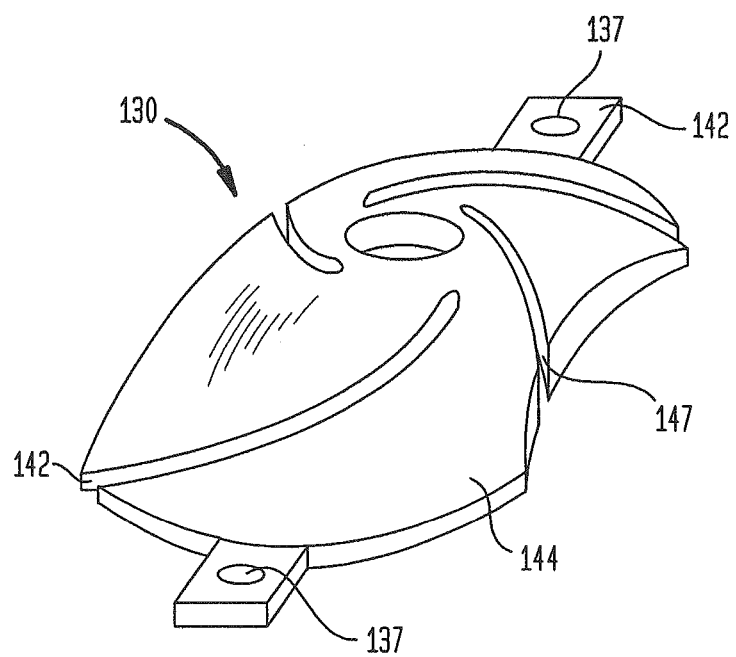
FIGS. 4a and 4b are a side perspective view and a cross section view of a lower plate having a slotted partial circular domed arch-shaped strip spring including a central socket mounted thereto it.
Figure 4B:
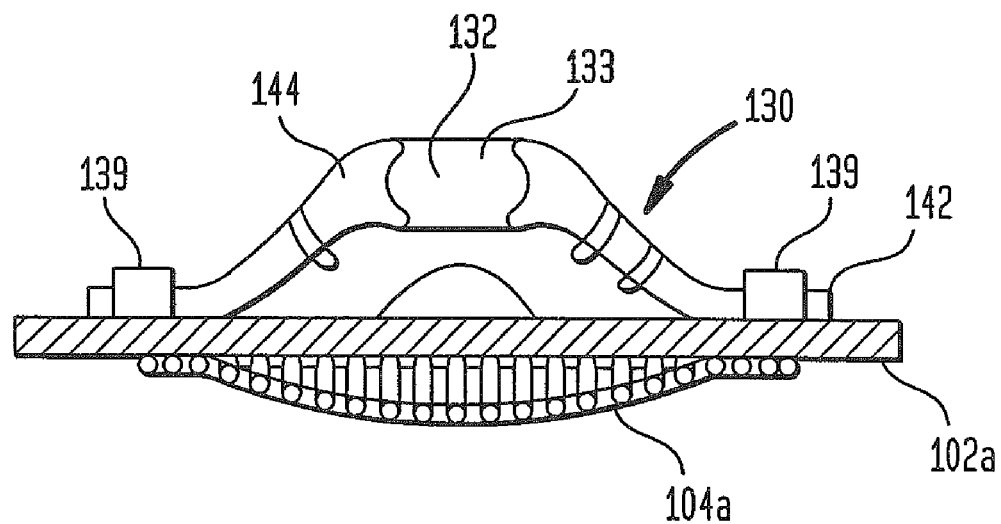

Referring now to FIGS. 4a and 4b, the partial circular domed slotted arch strip spring 130 of this embodiment is shown in a side view and a cross-section view, respectively.

As introduced above, the domed strip of metal comprise flat ends 142 and a partially circular domed central portion 144. The central portion 144 is curvate in two axes, and shall hereinafter be termed a domed arch 144. The central portion 144 is curved along the long axis (the length of the strip) of the strip into an upside down U-shape. The central portion 144 is further curved in the lateral direction (the width of the strip) such that the outer surface (the top of the upside down U-shape) is convex. Stated alternatively, the central curvate portion 144 of the metal strip comprises a section of a hemispheric shell (or paraboloid, or other suitable geometric shape) which has been cut along two minor arcs which are parallel to, but on opposing sides of a diameter (great circles) of the surface (thus removing two lateral edges of the domed shell).

The lateral ends 142 of the slotted domed arch springs include holes 137 through which set screws 139 may be introduced therethrough and into the set screw holes 111 in the plate 100a to secure the spring 130 to the plate. The slots 147 of the partial circular slotted domed arch spring 130 are provided to render the springs more deflectable, thus mimicking the natural behavior of the cartilage of the human intervertebral disc. The slots 147 are spirally disposed in the disc extending from the lateral edges of the central domed portion 144 to points which are out from the central hole 132 in the spring.

This partial circular domed arch strip spring 130 further includes the additional feature of having an enlarged central opening 132. This central opening 132 includes a curvate volume 133 for receiving therein the ball-shaped head 107 of the post 105 of the lower plate 100b described above. More particularly, the curvate volume 133 has a substantially constant radius of curvature which is also substantially equivalent to the radius of the ball-shaped head 107 of the post 105.

Figure 5:
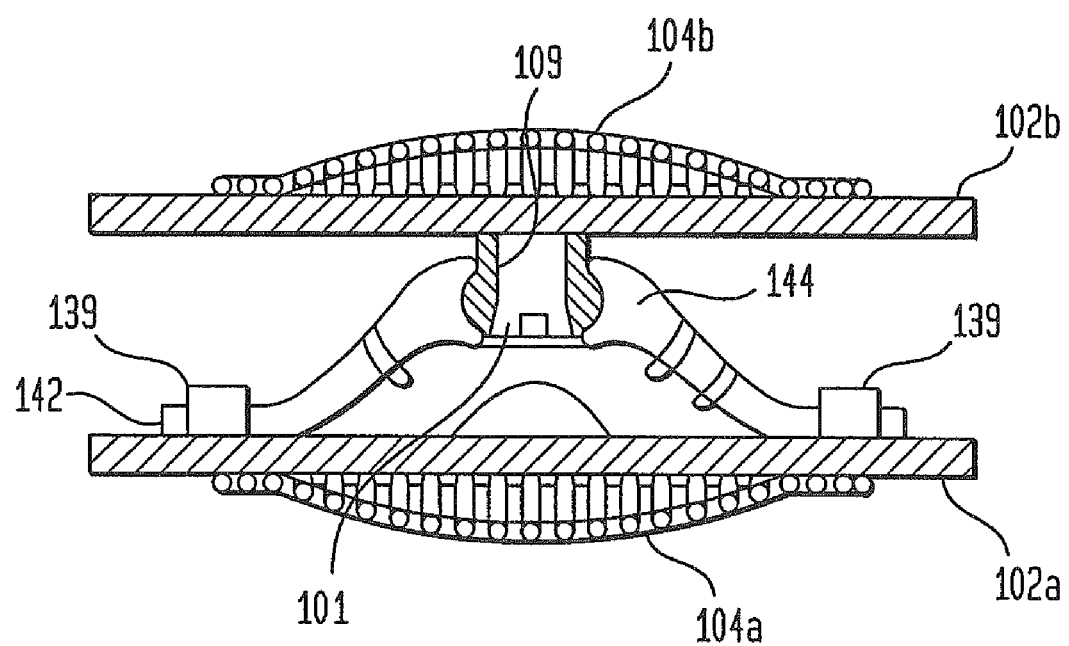
FIG. 5 is a side cross-section view of a second embodiment of the present invention which utilizes the elements shown in FIGS. 3a, 3b, 4a, and 4b.

Referring also to FIG. 5, in which the fully assembled second embodiment of the present invention is shown, the combination and assembly of this embodiment is now provided. The deflectability of the ball-shaped head 107 of the post 105, prior to the insertion of the set screw 101, permits the head 107 to be inserted into the interior volume 133 at the peak of the slotted domed arch strip spring 130. Subsequent introduction of the set screw 101 into the axial bore 109 of the post 101 flexibly couples the head 107 to the spring 130 by virtue of the head 107 not being compressible and removable from the central volume 133, but the post 105 being polyaxially retained in the socket 133. Ideally the post head 107 is locked loosely enough within the central volume 133 of the spring 130 such that anatomically relevant rotation of the plates 100a, 100b remains viable. In alternative variation, however, it is possible to design the coupling such that the locking of the set screw 101 in the head 107 locks the assembly in one rotational orientation, preventing free rotation of the plates relative to one another. A combined embodiment may be one in which the set screw 101 may be selectively positioned in an unlocked (but still securing for the purpose of retention) and a locked orientation.

While there has been described and illustrated embodiments of an intervertebral spacer device, it will be apparent to those skilled in the art that variations and modifications are possible without deviating from the broad spirit and principle of the present invention. The present invention shall, therefore, not be limited solely to the specific embodiments disclosed herein.

The invention claimed is:

1. An intervertebral spacer device comprising:
 a first plate having an inner surface and an exterior surface, the inner surface of the first plate including a post member extending substantially perpendicular therefrom, the post member including a ball-shaped head having a outer curved convex surface, the post member having a central threaded axial bore;

a second plate having an inner surface and an exterior surface, the inner surface of the first and second plates facing one another;

a wire mesh secured over one of the exterior surfaces of the first and second plates, wherein the mesh has a perimeter that is anchored to the exterior surface and a center, wherein only the center of the mesh is deflectable relative to the exterior surface of the one of the first and second plates; and a slotted domed arch strip spring having a top side with a partially circular convex surface, an underside with a partially circular concave surface, and a plurality of slots extending through the top side and underside of the spring, the spring further having a central opening including a concave volume, the spring having first and second lateral ends each having an aperture therethrough, the apertures adapted to receive a fastening member for fixing the lateral ends of the spring to the inner surface of the second plate, wherein the ball-shaped head of the post member is received within the central opening of the spring and is locked within the concave volume thereof when a fastening member is received and held within the central threaded axial bore of the post member.

2. The intervertebral spacer device of claim 1, wherein the one of the exterior surfaces includes a substantially flat region and the mesh overlies and is spaced from the substantially flat region.

3. The intervertebral spacer device of claim 2, wherein the mesh overlying the substantially flat region has a convex shape when in an undeflected state.

4. The intervertebral spacer device of claim 1, wherein the ball-shaped head of the post member is inwardly deflectable for being inserted into the central opening of the spring.

5. An intervertebral spacer device comprising:
a first plate having an inner surface and an exterior surface, the inner surface of the first plate including a post member extending substantially perpendicular therefrom, the post member including a ball-shaped head having an outer curved convex surface, the post member having a central threaded axial bore;

a second plate having an inner surface and an exterior surface, the inner surface of the first and second plates facing one another;

a wire mesh secured over one of the exterior surfaces of the first and second plates, wherein the mesh has a perimeter that is anchored to the exterior surface and a center, wherein only the center of the mesh is deflectable relative to the exterior surface of the one of the first and second plates; and a slotted domed arch strip spring having a top side with a partially circular convex surface facing toward the inner surface of the first plate, an underside with a partially circular concave surface facing toward the inner surface of the second plate, the spring further having a central opening including a concave volume; and a joint coupling the first and second plates together, the joint including the ball-shaped head of the post, the central opening of the spring, and a fastening member, wherein the ball-shaped head of the post member is received within the central opening of the spring and is locked within the concave volume thereof when the fastening member is received and held within the central threaded axial bore of the post member.

6. The intervertebral spacer device of claim 5, further comprising a plurality of slots extending through the top side and underside of the spring.

7. The intervertebral spacer device of claim 5, wherein the spring includes first and second lateral ends.

8. The intervertebral spacer device of claim 7, wherein the first and second lateral ends of the spring each have an aperture therethrough, the apertures adapted to receive a fastening member for fixing the lateral ends of the spring to the inner surface of the second plate.

9. The intervertebral spacer device of claim 5, wherein the ball-shaped head of the post member is inwardly deflectable for being inserted into the central opening of the spring.

* * * * *